United States Patent
Buzzetti et al.

Patent Number: 5,663,346
Date of Patent: Sep. 2, 1997

[54] SUBSTITUTED AZAINDOLYLIDENE COMPOUNDS AND PROCESS FOR THEIR PREPARATION

[75] Inventors: Franco Buzzetti, Monza; Maria Gabriella Brasca, Cusago; Antonio Longo, Milan; Dario Ballinari, San Donato Milanese, all of Italy

[73] Assignee: Pharmacia S.p.A., Milan, Italy

[21] Appl. No.: 592,297

[22] PCT Filed: May 30, 1995

[86] PCT No.: PCT/EP95/02043

§ 371 Date: Feb. 9, 1996

§ 102(e) Date: Feb. 9, 1996

[87] PCT Pub. No.: WO96/00226

PCT Pub. Date: Jan. 4, 1996

[30] Foreign Application Priority Data

Jun. 24, 1994 [GB] United Kingdom .......... 9412719

[51] Int. Cl.⁶ .......... C07D 471/02; C07D 403/02; C07D 405/02; A01N 43/34

[52] U.S. Cl. .......... 546/113; 544/373; 544/127

[58] Field of Search .......... 546/113; 514/300; 544/373, 127

[56] References Cited

FOREIGN PATENT DOCUMENTS 1141949  2/1967  United Kingdom .
9113055  9/1991  WIPO .

*Primary Examiner*—Matthew V. Grumbling
*Assistant Examiner*—Michael Bucknum
*Attorney, Agent, or Firm*—Oblon, Spivak, McClelland, Maier & Neustadt, P.C.

[57] ABSTRACT

The present invention relates to compounds useful as tyrosine kinase inhibitors, having the following general formula (I)

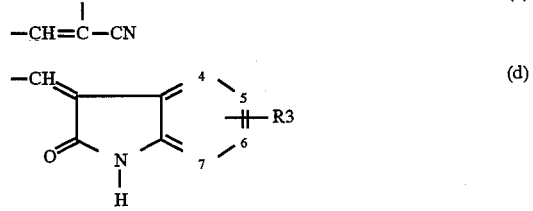

wherein
one of the groups $X^1$, $X^2$, $X^3$, $X^4$ is N and the others are CH; R is a group of formula (a), (b), (c) or (d)

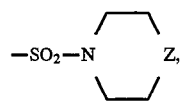

(a)

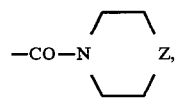

(b)

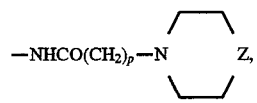

(c)

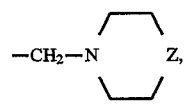

(d)

each of $R^1$ and $R^3$ independently is hydrogen, amino, carboxy, cyano, $-SO_3R^4$, $-SO_2NHR^5$,

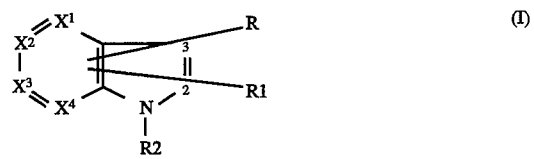

$-COOR^6$, $-CONH(CH_2)_oPh$, $-CONHCH_2(CHOH)_n CH_2OH$,

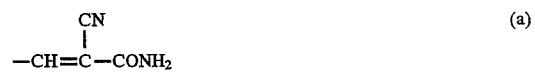

$-N(CH_2CH_2OH)_2$, $-NHCH_2(CHOH)_nCH_2OH$, $-NHCONH_2$, $-NHC(NH_2)=NH$, $-NHCO(CHOH)_nCH_2OH$,

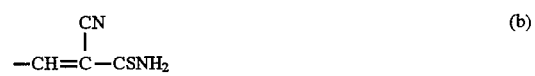

$-NHSO_2R^7$, $-OCH_2(CHOH)_nCH_2OH$, $-OOC(CHOH)_nCH_2OH$, $-OPO(OH)_2$, $-OCH_2SO_2NH_2$, $-CH_2NH_2$, $-C(NH_2)=NH$, $-CH_2NHC(NH_2)=NH$, $-CH_2OH$, $-CH_2OOC(CHOH)_nC_2OH$, $-CH_2OPO(OH)_2$, $-PO(OH)_2$;
$R^2$ is H, $C_1-C_6$ alkyl, $C_2-C_6$ alkanoyl, $-CH_2OH$, $-CH_2CH_2CONH_2$, $-SO_2Me$, $-COCH_2SO_2NH_2$;
$R^4$ is H, $-CH_2(CHOH)_nCH_2OH$, $C_1-C_6$ alkyl;
$R^5$ is H, $C_1-C_6$ alkyl, $-CH_2(CHOH)_nCH_2OH$, $-(CH_2)_mNMe_2$;
$R^6$ is $C_1-C_6$ alkyl, unsubstituted or substituted by phenyl, $-CH_2(CHOH)_nCH_2OH$;
$R^7$ is Me, $-C_6H_4Me$;
Z is $CH_2$, O, NH, $NCH_2CH_2OH$;
n is 1 or 1;
m is 2 or 3;
o is 0, 1, 2 or 3;
p is 1, 2 or 3;
provided that when R is (a), (b), or (c) then $R^1$ is not H and when R is (d) then one of $R^1$ and $R^3$ is not H; and the pharmaceutically acceptable salts thereof.

10 Claims, No Drawings

SUBSTITUTED AZAINDOLYLIDENE COMPOUNDS AND PROCESS FOR THEIR PREPARATION

The present invention relates to new substituted azaindolylidene compounds, to a process for their preparation, to pharmaceutical compositions containing them and to their use as therapeutic agents. The present invention provides compounds having the following general formula (I)

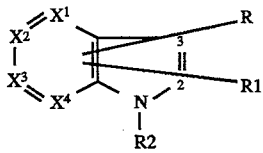

wherein one of the groups $X^1$, $X^2$, $X^3$ and $X^4$ is N and the others are CH; R is a group of formula (a), (b), (c) or (d)

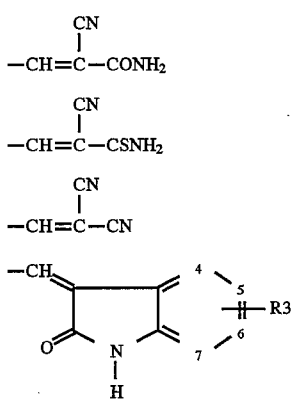

each of $R^1$ and $R^3$ independently, is hydrogen, amino, carboxy, cyano, $-SO_3R^4$, $-SO_2NHR^5$,

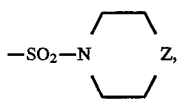

$-COOR^6$, $-CONH(CH_2)_oPh$, $-CONHCH_2(CHOH)_nCH_2OH$,

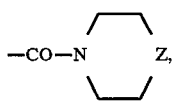

$-N(CH_2CH_2OH)_2$, $NHCH_2(CHOH)_nCH_2OH$, $-NHCONH_2$, $-NHC(NH_2)=NH$, $-NHCO(CHOH)_nCH_2OH$,

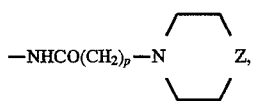

$-NHSO_2R^7$, $-OCH_2(CHOH)_nCH_2OH$, $-OOC(CHOH)_nCH_2OH$, $-OPO(OH)_2$, $-OCH_2SO_2NH_2$, $-CH_2NH_2$, $-C(NH_2)=NH$, $-CH_2NHC(NH_2)=NH$,

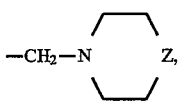

$-CH_2OH$, $-CH_2OOC(CHOH)_nCH_2OH$, $-CH_2OPO(OH)_2$, $-PO(OH)_2$;

$R^2$ is H, $C_1$-$C_6$ alkanoyl, $-CH_2OH$, $-CH_2CH_2CONH_2$, $-SO_2Me$, $-COCH_2SO_2NH_2$;

$R^4$ is H, $-CH_2(CHOH)_nCH_2OH$, $C_1$-$C_6$ alkyl;

$R^5$ is H, $C_1$-$C_6$ alkyl, $-CH_2(CHOH)_nCH_2OH$, $-(CH_2)_mNMe_2$;

$R^6$ is $C_1$-$C_6$ alkyl, unsubstituted or substituted by phenyl, $-CH_2(CHOH)_nCH_2OH$;

$R^7$ is Me, $-C_6H_4Me$;

Z is $CH_2$, O, NH, $NCH_2CH_2OH$;

n is 0 or 1;

m is 2 or 3;

o is 0, 1, 2 or 3;

p is 1, 2 or 3;

provided that when R is (a), (b), or (c) then $R^1$ is not H and when R is (d) then one of $R^1$ and $R^3$ is not H; and the pharmaceutically acceptable salts thereof. In the compounds of the invention each of the substituents R and $R^1$ may be independently on either of the pyridine or pyrrole moieties of the bicyclic azaindole ring. The invention includes within its scope all the possible isomers, stereoisomers, in particular Z- and E-isomers and their mixtures, and the metabolites and the metabolic precursors or bio-precursors (otherwise known as pro-drugs) of the compounds of formula (I). The substituent R is preferably linked the position 2 or 3 of the azaindole ring, in particular to position 3. The substituent $R^1$ is preferably on the pyridine moiety. Preferably one of $R^1$ and $R^3$ is hydrogen whereas the other not hydrogen. The $R^3$ substituent is preferably in the 5-position of the oxindole ring (d). The alkyl group and the alkyl moiety in the alkanoyl group may be branched or straight alkyl chain. A $C_1$-$C_6$ alkyl group is preferably a $C_1$-$C_4$ alkyl group, e.g. methyl, ethyl, propyl, isopropyl, butyl, sec-butyl or t-butyl, in particular methyl or ethyl. A $C_2$-$C_6$ alkanoyl group is preferably a $C_2$-$C_3$ alkanoyl group, in particular acetyl or propionyl. Pharmaceutically acceptable salts of the compounds of the invention include acid addition salts with inorganic, e.g. nitric, hydrochloric, hydrobromic, sulphuric, perchloric and phosphoric acids or organic, e.g. acetic, trifluoroacetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium bases or alkaline-earth metal, especially calcium or magnesium bases, or with organic bases, e.g. acyclic or cyclic amines, preferably triethylamine or piperidine. As stated above, the present invention also includes with in its scope pharmaceutically acceptable bio-precursors (otherwise known as pro-drugs) of the calmpounds of formula (I), i.e. compounds which have a different formula to formula (I) above but which, nevertheless, upon administration to a human being are converted directly or indirectly in vivo into a compound of formula (I).

Preferred compounds of the invention are the compounds of formula (I), wherein $X^1$, $X^2$, $X^3$ ahd $X^4$ are as defined above;

R is as defined above and is linked in position 2 or 3 of the azaindole ring;

$R^2$ is hydrogen or $C_1$-$C_4$ alkyl; each of $R^1$ and $R^3$, independently, is hydrogen, amino, carboxy, cyano, $-SO_3H$, $-SO_2NH_2$,

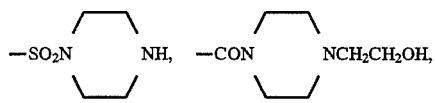

—COOMe, —N(CH₂CH₂OH)₂, —NH—CH₂—CHOH—CH₂OH, —NHCONH₂, —NHC(NH₂)=NH, —NHCOHOHCH₂OH,

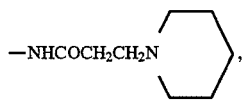

—NHSO₂Me, —OCH₂CHOHCH₂OH, —OOC—CH₂OH, —OOCCHOHCH₂OH, —OPO(OH)₂, —CH₂NH₂, —C(NH₂)=NH,

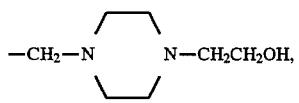

—CH₂OH, —CH₂PO(OH)₂, —PO(OH)₂,
provided that when R is not (a), (b) or (c) then R¹ is not hydrogen and when R is (d) then one of R¹ and R³ is not hydrogen, and the pharmaceutically acceptable salt thereof.

More preferred compounds of the invention are the compounds of formula (I) in which X¹, X², X³ and X⁴ are as defined above;

R is as defined above and is linked in position 3 of the azaindole ring;

R² is hydrogen; each of R¹ and R³ independently is hydrogen, amino, carboxy, cyano, —SO₃H, —SO₂NH₂

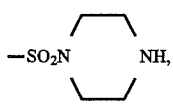

—N(CH₂CH₂OH)₂, —NHCONH₂, —NHC(NH₂)=NH,

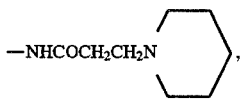

—NHSO₂Me, —OCH₂CHOHCH₂OH, —OOCCHOHCH₂OH, —CH₂NH₂, —C(NH₂)=NH, —CH₂OH, —PO(OH)₂, and R³ is preferably linked at position 5 of the oxindole ring; provided that when R is (a), (b) or (c) then R¹ is not hydrogen and when R is (d) then one of R¹ and R³ is not hydrogen, and the pharmaceutically acceptable salt thereof.

Examples of specific compounds of the invention are the following compounds, which, when appropriate, may be either Z- or E-diastereomers or Z,E-mixtures of said diastereomers:

2-cyano-3-(4-sulfo-7-azaindol-3-yl)acrylamide, sodium salt;
2-cyano-3-[(N,N-piperazinyl-4-sulfamoyl)-7-azaindol-3-yl]acrylamide;
2-cyano-3-(4-ureido-7-azaindol-3-yl)acrylamide;
2-cyano-3-(4-glyceroylamido-7-azaindol-3-yl)acrylamide;
2-cyano-3-[4-(3-piperidinopropionylamino)-7-azaindol-3-yl]acrylamide;
2-cyano-3-(4-mesylamino-7-azaindol-3-yl)acrylamide;
2-cyano-3-[4-(2,3-dihydroxypropoxy)-7-azaindol-3-yl]acrylamide;
2-cyano-3-(4-aminomethyl-7-azaindol-3-yl)acrylamide;
2-cyano-3-(4-amidino-7-azaindol-3-yl)acrylamide;
2-cyano-3-(4-sulfo-7-azaindol-3-yl)thioacrylamide, sodium salt;
2-cyano-3-[(N,N-piperazinyl-4-sulfamoyl)-7-azaindol-3-yl]thioacrylamide;
2-cyano-3-(4-ureido-7-azaindol-3-yl)thioacrylamide;
2-cyano-3-(4-glyceroylamido-7-azaindol-3-yl)thioacrylamide;
2-cyano-3-[4-(3-piperidinopropionylamino)-7-azaindol-3-yl]thioacrylamide;
2-cyano-3-(4-mesylamino-7-azaindol-3-yl)thioacrylamide;
2-cyano-3-[4-(2,3-dihydroxypropoxy)-7-azaindol-3-yl]thioacrylamide;
2-cyano-3-(4-aminomethyl-7-azaindol-3-yl)thioacrylamide;
2-cyano-3-(4-amidino-7-azaindol-3-yl)thioacrylamide;
2-cyano-3-(4-sulfo-7-azaindol-3-yl)acrylonitrile, sodium salt;
2-cyano-3-[(N,N-piperazinyl-4-sulfamoyl)-7-azaindol-3-yl]acrylonitrile;
2-cyano-3-(4-ureido-7-azaindol-3-yl) acrylonitrile;
2-cyano-3-(4-glyceroylamido-7-azaindol-3-yl)acrylonitrile;
2-cyano-3-[4-(3-piperidinopropionylamino)-7-azaindol-3-yl]acrylonitrile;
2-cyano-3-(4-mesylamino-7-azaindol-3-yl)acrylonitrile;
2-cyano-3-[4-(2,3-dihydroxypropoxy)-7-azaindol-3-yl]acrylonitrile;
2-cyano-3-(4-aminomethyl-7-azaindol-3-yl)acrylonitrile;
2-cyano-3-(4-amidino-7-azaindol-3-yl)acrylonitrile;
3-[(7-azaindol-3-yl)methylen]-2-oxindole-5-sulfonic acid, sodium salt;
5-sulfamoyl-3-[(7-azaindol-3-yl)methylen]oxindole;
5-(N,N-piperazinylsulfamoyl)-3-[(7-azaindol-3-yl)methylen]-2-oxindole;
5-[N,N-[4-(2-hydroxyethyl)piperazinylsulfamoyl]-3-[(7-azaindol-3-yl)methylen]-2-oxindole;
5-diethanolamino-3-[(7-azaindol-3-yl)methylen]-2-oxindole;
5-ureido-3-[(7-azaindol-3-yl)methylen]-2-oxindole;
5-guanidino3-[(7-azaindol-3-yl)methylen]-2-oxindole;
5-glyceroylamido-3-[(7-azaindol-3-yl)methylen]-2-oxindole;
5-(3-piperidinopropionylamino)-3-[(7-azaindol-3-yl)methylen]-2-oxindole, dihydrochloride;
5-mesylamino-3-[(7-azaindol-3-yl)methylen]-2-oxindole;
5-(2,3-dihydroxypropoxy)-3-[(7-azaindol-3-yl)methylen]-2-oxindole;
5-glyceroyloxy-3-[(7-azaindol-3-yl)methylen]-2-oxindole;
3-[(7-azaindol-3-yl)methylen]-2-oxindol-5-yl-phosphate;
5-aminomethyl-3-[(7-azaindol-3-yl)methylen]-2-oxindole;
5-amidino3-[(7-azaindol-3-yl)methylen]-2-oxindole;
5-(2,3-dihydroxypropylamine)-3-[(7-azaindol-3-yl)methylen]-2-oxindole;
5-carbomethoxy-3-[(7-azaindol-3-yl)methylen]-2-oxindole;
5-[4-(2-hydroxyethyl)-1-piperazinylmethyl]-3-[(7-azaindol-3-yl)methylen]-2-oxindole;
5-[N,N-[4-(2-hydroxyethyl)piperazinylcarbamoyl]-3-[(7-azaindol-3-yl)methylen]-2-oxindole;
5-glycoloyloxyl-3-[(7-azaindol-3-yl)methylen]-2-oxindole;
5-amino-3-[(7-azaindol,3-yl)methylen]-2-oxindole, ditrifluoroacetate;
5-carboxy-3-[(7-azaindol-3-yl)methylen]-2-oxindole, piperidinium salt;
5-cyano-3-[(7-azaindol-3-yl)methylen]-2-oxindole;
5-carboethoxy-3-[(7-azaindol-3-yl)methylen]-2-oxindole;
5-carbobenzyloxy-3-[(7-azaindol-3-yl)methylen]-2-oxindole;

5-carbophenylethyloxy-3-[(7-azaindol-3-yl)methylen]-2-oxindole;

5-phenylcarbamoyl-3-[(7-azaindol-3-yl)methylen]-2-oxindole;

5-benzylcarbamoyl-3-[(7-azaindol-3-yl)methylen]-2-oxindole;

as well as the free compounds corresponding to the above listed salified compounds and the pharmaceutically acceptable salts of the above listed free compounds.

The compounds of the invention, and the pharmaceutically acceptable salts thereof, can be obtained by a process comprising:

a) condensation of an aldehyde of formula (II)

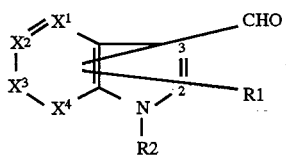

wherein $X^1$, $X^2$, $X^3$, $X^4$, $R^1$ and $R^2$ are as defined above, with a compound of formula (a'), (b'), (c') or (d'), respectively:

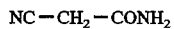 (a')

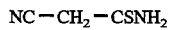 (b')

 (c')

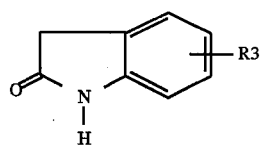 (d')

wherein $R^3$ is as defined above. Each of the substituents $R^1$ and —CHO in a compound of formula (II) may be, independently, on either of the pyridine or pyrrole moiety; or b) N-alkylation of a compound of formula (III)

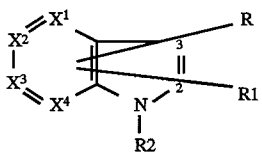 (III)

wherein either $R^1$ and $R^3$ are both amino of one of $R^1$ and $R^3$ is amino and the other is hydrogen, if it is present, and $X^1$, $X^2$, $X^3$, $X^4$, R and $R^2$ are as defined above, thus obtaining, a compound of formula (I) wherein either $R^1$ and $R^3$ are both —N(CH$_2$CH$_2$OH)$_2$ or —NHCH$_2$(CHOH)$_n$CH$_2$OH, or one is —N(CH$_2$CH$_2$OH)$_2$ or —NHCH$_2$(CHOH)$_n$CH$_2$OH and the other is hydrogen, if it is present, and n, $X^1$, $X^2$, $X^3$, $X^4$, R and $R^2$ are as defined above; or c) N-acylation of a compound of formula (III) wherein either $R^1$ and $R^3$ are both amino or one of $R^1$ and $R^3$ is amino and the other is hydrogen, if it is present, and $X^1$, $X^2$, $X^3$, $X^4$, R and $R^2$ are as defined above, thus obtaining a compound of formula (I) wherein either $R^1$ and $R^3$ are both —NHCO(CHOH)$_n$CH$_2$OH or

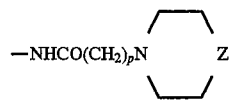

or one is —NHCO(CHOH)$_n$CH$_2$OH or

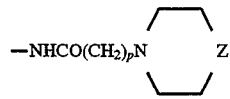

and the other is hydrogen, if it is present, n, p, Z, $X^1$, $X^2$, $X^3$, $X^4$, R and $R^2$ are as defined above; or d) N-sulfonylation of a compound of formula (III) wherein either $R^1$ and $R^3$ are both amino or one of $R^1$ and $R^3$ is amino and the other is hydrogen, if it is present, and $X^1$, $X^2$, $X^3$, $X^4$, R and $R^2$ are as defined above, thus obtaining a compound of formula (I) wherein either $R^1$ and $R^3$ are both —NHSO$_2$R$^7$ or one of $R^1$ and $R^3$ is —NHSO$_2$R$^7$ and the other is hydrogen, if it is present, and $R^7$, $X^1$, $X^2$, $X^3$, $X^4$, R and $R^2$ are as defined above; or e) N-amidination of a compound of formula (III) wherein either $R^1$ and $R^3$ are both amino or one of $R^1$ and $R^3$ is amino and the other is hydrogen, if it is present, and $X^1$, $X^2$, $X^3$, $X^4$, R and $R^2$ are as defined above, thus obtaining a compound of formula (I) wherein either $R^1$ and $R^3$ are both —NHC(NH$_2$)=NH or one of $R^1$ and $R^3$ is —NHC(NH$_2$)=NH and the other is hydrogen, if it, is present, and $X^1$, $X^2$, $X^3$, $X^4$, R and $R^2$ are as defined above; or f) N-carbamoylation of a compound of formula (III) wherein either $R^1$ and $R^3$ are both amino or one of $R^1$ and $R^3$ is amino and the other is hydrogen, if it is present, and $X^1$, $X^2$, $X^3$, $X^4$, R and $R^2$ are as defined above, thus obtaining a compound of formula (I) wherein either $R^1$ and $R^3$ are both —NHCONH$_2$ or one of $R^1$ and $R^3$ is —NHCONH$_2$ and the other is hydrogen, if it is present, and $X^1$, $X^2$, $X^3$, $X^4$, R and $R^2$ are as defined above; or g) O-alkylation of a compound of formula (III) wherein either $R^1$ and $R^3$ are both hydroxy or one of $R^1$ and $R^3$ is hydroxy and the other is hydrogen, if it is present, and $X^1$, $X^2$, $X^3$, $X^4$, R and $R^2$ are as defined above, thus obtaining a compound of formula (I) wherein either $R^1$ and $R^3$ are both —OCH$_2$(CHOH)$_n$CH$_2$OH or —OCH$_2$SO$_2$NH$_2$ or one of $R^1$ and $R^3$ is —OCH$_2$(CHOH)$_n$CH$_2$OH or —OCH$_2$SO$_2$NH$_2$ and the other is hydrogen, if it is present, and n, $X^1$, $X^2$, $X^3$, $X^4$, R and $R^2$ are as defined above; or h) O-acylation of a compound of formula (III) wherein either $R^1$ and $R^3$ are both hydroxy or one of $R^1$ and $R^3$ is hydroxy and the other is hydrogen, if it is present, and $X^1$, $X^2$, $X^3$, $X^4$, R and $R^2$ are as defined above, thus obtaining a compound of formula (I) wherein either $R^1$ and $R^3$ are both —OOC(CHOH)$_n$CH$_2$OH or one of $R^1$ and $R^3$ is —OOC(CHOH)$_n$CH$_2$OH and the other is hydrogen, if it is present, and n, $X^1$, $X^2$, $X^3$, $X^4$, R and $R^2$ are as defined above; or i) O-phosphorylation of a compound of formula (III) wherein either $R^1$ and $R^3$ are both hydroxy or one of $R^1$ and $R^3$ is hydroxy and the other is hydrogen, if it is present, and $X^1$, $X^2$, $X^3$, $X^4$, R and $R^2$ are as defined above, thus obtaining a compound of formula (I)

wherein either $R^1$ and $R^3$ are both —OPO(OH)$_2$ or one of $R^1$ and $R^3$ is —OPO(OH)$_2$ and the other is hydrogen, if it is present, and $X^1$, $X^2$, $X^3$, $X^4$, R and $R^2$ are as defined above; or k) esterification of a compound of formula (III) wherein either $R^1$ and $R^3$ are both carboxy or one of $R^1$ and $R^3$ is carboxy and the other is hydrogen, if it is present, and $X^1$, $X^2$, $X^3$, $X^4$, R and $R^2$ are as defined above, thus obtaining a compound of formula (I) wherein either $R^1$ and $R^3$ are both —COOR$^6$ or one of $R^1$ and $R^3$ is —COOR$^6$ and the other is hydrogen, if it is, present and $R^6$, $X^1$, $X^2$, $X^3$, $X^4$, R and $R^2$ are as defined above; or l) ammonia addition to a compound of formula (III) wherein either $R^1$ and $R^3$ are both —C≡N or one of $R^1$ and $R^3$ is —C≡N and the other is hydrogen, if it is present, and $X^1$, $X^2$, $X^3$, $X^4$, R and $R^2$ are as defined above, thus obtaining compound of formula (I) wherein either $R^1$ and $R^3$ are both —C(NH$_2$)=NH or one of $R^1$ and $R^3$ is —C(NH$_2$)=NH and the other is hydrogen, if it is present, and $X^1$, $X^2$, $X^3$, $X^4$, R and $R^2$ are as defined above; or m) amination of a compound of formula (III) wherein either $R^1$ and $R^3$ are both —CH$_2$Cl or one of $R^1$ and $R^3$ is —CH$_2$Cl and the other is hydrogen, if it is present, and $X^1$, $X^2$, $X^3$, $X^4$, R and $R^2$ are as defined above; thus obtaining a substituted compound of formula (I) wherein either $R^1$ and $R^3$ are both

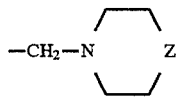

or one of $R^1$ and $R^3$ is

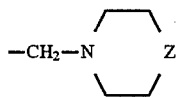

and the other is hydrogen, if it is present, and Z, $X^1$, $X^2$, $X^3$, $X^4$, R and $R^2$ are ss defined above;

and/or conversion,of a compound of formula (I) into another ompound of formula (I) and/or optional salification of a compound of formula (I) or conversion of a salt into the corresponding free compound of formula (I) and/or, if desired, separation of a mixture of isomers into the single isomers.

The reaction of a compound of formula (II) with a compound of formula (a'), (b'), (c') or (d') according to the process step a), may be carried out according to known methods, as herebelow described; preferably in the presence of a basic catalyst, e.g. pyridine, piperidine, dimethylamine, or a suitable alkali metal hydroxide or alkoxide. For example the reaction of a compound of formula (II) with a compound of formula (a'), (b'), (c') or (d'), respectively, may be carried out under the conditions of the Knoevenagel reaction as described, e.g., by G. Jones in Organic Reactions 15, 204 (1967). Suitable catalysts are organic bases such as pyridine, piperidine or diethylamine. The condensation may be performed in an inert organic solvent, e.g. pyridine, ethanol, methanol, benzene or dioxane at temperatures ranging from about 0° C. to about 100° C. Preferably the reaction is carried out in warm ethanol solution in the presence of piperidine catalyst.

The N-alkylation according to process step b) may be carried out according to known methods, e.g. as described in Houben-Weyl, Methoden der Organischen Chemie, Vol. XI/I, page 311 (1957). Thus, the aromatic amine is reacted with ethylene oxide in water, alcoholic or hydroalcoholic solution at temperatures from, e.g., 0° C. to 100° C. Preferably the reaction is carried out in hydroalcoholic suspension at about 70°-80° C. by introducing ethylene oxide gas. On the other hand the N-alkylation according to process step b) in order to obtain compounds of formula (I) wherein $R^1$ and/or $R^3$ is —NHCH$_2$(CHOH)$_n$CH$_2$OH can be carried out by reductive amination, i.e. by condensation with an aldehyde of formula CH$_2$OH(CHOH)$_n$CHO in the presence of a reducing agent, e.g. as described by Tietze and Eiche in Reactions and Synthesis in the Organic Chemistry Laboratory (1988) at page 77. Thus, to the alcoholic solution of the aromatic amine and the aldehyde is added portionwise sodium cyanoborohydride at temperatures ranging from 0° C. to reflux temperature.

The N-acylation according to process step c) may be carried out by known methods, e.g. as described in Houben-Weyl, Vol. E5, part. II, page 960 (1985). Thus, the aromatic amine is reacted with the corresponding carboxylic acid of formula CH$_2$OH(CHOH)$_n$COOH or

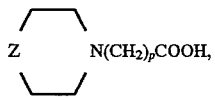

wherein Z, p and n are as defined above by using a condensing agent, such as dicyclohexylcarbodiimide (DCCD). Preferably equimolar amounts of amine, carboxylic acid and dicyclohexylcarbodiimide are used in an inert solvent such as THF or benzene at temperatures from about 0° to 50° C.

The N-sulfonylation according to process step d) may be carried out by known methods, e.g. as described in Houben-Weyl, vol. IX, page 609 (1955). Thus, equimolar amounts of aromatic amine and sulfochloride of general formula $R^5$—SO$_2$—Cl are reacted in pyridine solution at temperatures from, e.g., −10° C. to 50° C.

The N-amidination according to process step e) may be carried out, e.g., as described by P. D. Davis et al. in J. Med. Chem. 1992, 35, 994. Thus, the aromatic amine is treated with about 1.5 molar equivalents 3,5-dimethylpyrazole-1-carboxamidine in refluxing ethanol in the presence of about 1 molar equlvalents of NaHCO$_3$.

The N-carbamoylation according to pprocess step f) may be carried out, e.g., as described in Houben-Weyl, vol. E4, page 362 (1983). Thus, the aromatic amine salt, preferably the hydrochloride salt, is reacted with an alkali metal cyanate, preferably NaOCN or KOCN, in aqueous or hydroalcoholic solution at temperatures ranging, e.g., from about 50° C. to about 100° C.

The O-alkylation according to process step g) may be carried out, e.g., as described in Houben-Weyl, Vol. VI/3, page 54 (1965). Thus, the phenol is first transformed into an alkali metal phenolate by treatment with an alkali metal alcoholate or hydroxide or amide. Then the phenolate is reacted with a halogenide of general formula XCH$_2$(CHOH)$_n$CH$_2$OH or XCH$_2$SO$_2$NH$_2$ (wherein X is chlorine or bromine) in an inert solvent such as benzene and THF at temperatures ranging from room to reflux temperature. Preferably the reaction is carried out in benzene solution by reacting the phenol first with a stoechiometric amount of NaNH$_2$ at room temperature and thin with an excess of halogenide at reflux temperature.

The O-acylation according to process step h) may be carried out by known methods, e.g. as described in Houben- Weyl, Vol. VIII, page 543 (1952). Thus, the phenol is reacted with the acid halide of general formula $CH_2OH(CHOH)_nCOCl$ in the presence of an organic base such as pyridine or triethylamine at temperatures ranging, e.g., from about 0° C. to about 50° C. Alternatively the phenol is reacted with the acid $CH_2OH(CHOH)_nCOOH$ in the presence of a condensing agent such as dicyclohexylcarbodiimide (DCCD). Preferably equimolar amounts of phenol and DCCD are used and the reaction is conducted in an inert solvent such as THF or benzene at temperatures from about 0° C. to about 50° C.

The O-phosphorylation according to process step i) may be carried out by known methods, e.g. as described in Houben-Weyl, vol. XII/2, page 143 (1964). Thus, the phenol is reacted with phosphoric acid or a derivative thereof in water or hydroalcoholic solution at temperature ranging from room to reflux temperature. Preferably the reaction is carried out in polyphosphoric acid (mixture of phosphoric acid and $P_2O_5$) which acts as reactant and solvent at temperatures ranging from about 50° C. to about 100° C.

The esterification according to process step k) may be carried out by well known methods, e.g. as described in Houben-Weyl, vol. VIII, page 508 (1952). Thus, the mixture of acid and alcohol, dissolved in an inert solvent such as benzene or chloroform, is heated to reflux in the presence of a mineral acid such as $H_2SO_4$ or HCl. Preferably the water formed is removed by azeotropic distillation in a Dean-Stark condenser.

The nitril transformation according to process step 1) may be carried out by known methods, e.g. as described in Houben-Weyl, vol. 8, page 697 and 702 (1952). Thus, to the ether or chloroform solution of the nitril is added an equimolar amount of ethanol and the resulting solution is saturated with HCl gas. The resulting iminoether hydrochloride is then transformed into amidine by reaction with ammonia in absolute ethanol at room temperature.

The amination according to process step m) may be carried out by known methods, e.g. as described in Houben-Weyl, vol. II/I, page 24 (1957). Thus, a mixture of the chloromethylene and piperazine compound is heated to a temperature from, e.g., about 50° C. to about 150° C. until the reaction is complete.

The optional salification of a compound of formula (I) as well as the conversion of a salt into the corresponding free compound and the separation of a mixtura of isomers into the single isomers as well as the conversion of a compound of formula (I) into another compound of formula (I) may be carried out according to known methods.

For example, the amidation of a compound of formula (I), wherein $R^1$ and/or $R^3$ is —$SO_3H$, so as to obtain a compound of formula (I), wherein $R^1$ and/or $R^3$ is —$SO_2NHR^5$ or

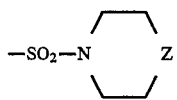

may be carried out by known methods as described above at process step d).

The conversion of a compound of formula (I) in which $R^1$ and/or $R^3$ is —$SO_3H$ into the corresponding compound of formula (I) wherein $R^1$ and/or $R^3$ is —$SO_3R^4$ may be carried out by known esterification methods, e.g. as described above at process step k).

The conversion of a compound of formula (I) in which $R^1$ and/or $R^3$ is —$CH_2NH_2$ into the corresponding compound of formula (I) wherein $R^1$ and/or $R^3$ is —$CH_2NH$—$C(NH_2)$=NH may be carried out by known amidination methods, e.g. as described above at process step e).

The esterification of a compound of formula (I) wherein $R^1$ and/or $R^3$ is —$CH_2OH$ in order to obtain a compound of formula (I) wherein $R^1$ and/or $R^3$ is —$CH_2OOC(CHOH)_nCH_2OH$ may be carried out as described above at process step k).

The conversion of a compound of formula (I) in which $R^1$ and/or $R^3$ is —$CH_2OH$ into the corresponding compound of formula (I) wherein $R^1$ and/or $R^3$ is —$CH_2OPO(OH)_2$ may be carried out as described above at process step i).

The conversion of a compound of formula (I) wherein $R^1$ and/or $R^3$ is —$COOR^6$ and wherein $R^6$ is preferably methyl into the corresponding compound of formula (I) wherein $R^1$ and/or $R^3$ is

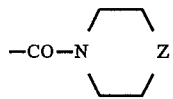

may be carried out by aminolysis, e.g. as described in Houben-Weyl, vol. E2, page 983 (1985). Preferably a mixture of the carbomethoxy compound and the amine compound of formula

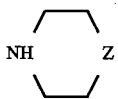

is heated to reflux and the formed methanol is removed continuously by distillation.

The optional salification of a compound of formula (I) as well as the conversion of a salt into the free compound and the separation of a mixture of isomers into the single isomers may be carried out by conventional methods. For example, the separation of a mixture of geometric isomers, e.g. cis- and trans-isomers, may be carried out by fractional crystallization from a suitable solvent or by chromatography, either column chromatography or high pressure liquid chromatography.

The compounds of formula (II) may be obtained according to known methods from compounds of formula (IV)

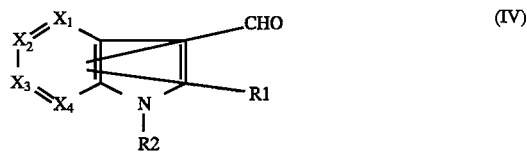

wherein $X^1$, $X^2$, $X^3$, $X^4$, $R^1$ and $R^2$ are as defined above.

For example, the 3-formylazaindole derivative of formula (IV) can be obtained from a compound of formula (V) by formylation with N-methyl-formanilide or DMF and phosphorous oxychloride according to the well known Vilsmeyer-Haack method (for a review see W. G. Jackson et al. in J. Am. Chem., Soc, 103, 533, 1981). The 2-formylazaindole derivatives are obtained when the 3-position is occupied.

The compounds of formuia (IV) are known or may be obtained by known methods from known compounds. For example, according to R. R. Lorenz et al. (J. Org. chem. 1965, 30, 2531) the various parent azaindoles (IVa) may be obtained following the 3-step process herebelow depicted starting from the appropriate aminomethylpyridine (V) via the formimidates (VI) and the formamidines (VII).

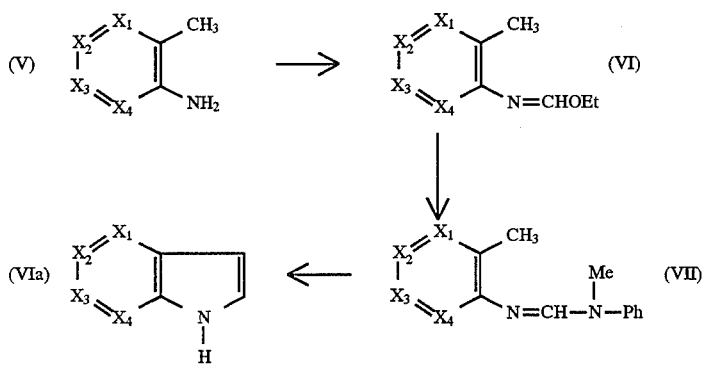

Thus 7-azaindole (IVa, $X^4=N$, $X^1=X^2=X^3=CH$) is obtained from 2-amino-3-methylpyridine (V, $X^4=N$, $X^1=X^2=X^3=CH$) whilst 4-amino-3-methylpyridine (V, $X^2=N$, $X^1=X^3=X^4=CH$) gives rise to 5-azaindole (IVa, $X^2=N$, $X^1=X^3=X^4=CH$). The 4-azaindole (IVa, $X^1=N$, $X^2=X^3=X^4=CH$) is obtained from 3-amino-2-methylpyridine (V, $X^1=N$, $X^2=X^3=X^4=CH$).

A compound of formula (III) wherein either $R^1$ and $R^3$ are both amino, hydroxy, carboxy, cyano, chloromethyl or sulfonic acid or one of $R^1$ and $R^3$ is amino, hydroxy, carboxy, cyano, chloromethyl or sulfonic acid and the other is hydrogen, if it is present, and $X^1$, $X^2$, $X^3$, $X^4$, R and $R^2$ are as defined above, can be obtained by condensation of a compound of formula (II) wherein $R^1$ is hydrogen, amino, hydroxy, carboxy, cyano, chloromethyl or sulfonic acid and $X^1$, $X^2$, $X^3$, $X^4$, and $R^2$ are as defined above, with a compound of formula (a'), (b'), (c') or (d') wherein in the latter case, $R^3$ is hydrogen, amino, hydroxy, carboxy, cyano, chloromethyl or sulfonic acid. The compounds of formula (a'), (b'), (c') and (d') are known or may be obtained by known methods from known compounds. When in the new compounds of the present invention and in the intermediate products used for their preparation groups are present which need to be protected before submitting them to the hereabove illustrated reactions, they may be protected before the reaction takes place and then deprotected at the end of the reaction, according to well known methods in organic chemistry.

PHARMACOLOGY

The compounds of the invention possess specific tyrosine kinase inhibiting activity. It is believed that tyrosine kinase inhibitors may be of great importance in the control of uncontrollea cellular reproduction, i.e. in cellular reproduction disorders. Hence the compounds according to the present invention can be useful in the treatment of pathological proliferation disorders in mammals, including humans. Typical examples of such disorders are tumors, including leukemia, and psoriasis. The compounds of the invention can also be useful in inhibiting the development of the atheromatous plaque and in the control of angiogenesis and as anti-metastatic agents. Recent studies on the molecular basis of neoplastic transformation have identified a family of genes, designed oncogenes, whose aberrant expression causes tumorigenesis. For example, the RNA tumor viruses possess such an oncogene sequence whost expression determines neoplastic conversion of infected cells. Several of their oncogene-encoded proteins, such as $pp60^{v-src}$, $p70^{gag-yes}$, $p130^{gag-fps}$ and $p70^{gag-fgr}$ display protein tyrosine kinase activity, that is they catalyse the transfer of the g-phosphate from adenosine triphosphate (ATP) to tyrosine residues in protein substrate. In normal cells, several growth factor receptors, for example the receptors for PDGF, EGF, aTGF and insulin, display tyrosine kinase activity.

Binding of the growth factor (GF) activates the receptors tyrosine kinase to undergo autophosphorylation and to phosphorylate closely adjacent molecules on tyrosine. Therefore, it is thought that the phosphorylation of these tyrosine kinase receptors plays an important role in signal transduction and that the principal function of tyrosine kinase activity in normal cells is to regulate cell growth. Perturbation of this activity by oncogenic tyrosine kinases that are either overproduced and/or display altered substrate specificity may cause loss of growth control and/or neoplastic transformation. Accordingly, a specific inhibitor of tyrosine kinase can be useful in investigating the mechanism of cancerogenesis, cell proliferation and differentiations and it can be effective in prevention and chemotherapy of cancer and in other pathological proliferative conditions, for instance as mentioned above. The tyrosine specific protein kinase activity of the compounds of the invention is shown, e.g., by the fact that they are active in the in-vitro and ln-vivo test described herebelow.

In-vitro Assay
p45 v-abl Kinase Purification

The enzyme used in our test was the p45 v-abl tyrosine kinase which represents the catalytic domain of the Abelson tyrosine kinase (isolated from the Abelson murine leukemia virus). The p45 v-abl kinase was produced and isolated as described by Wang et al. in J. Biol. chem 260, 64 (1985) and by Ferguson et al. in J. Biol. Chem 260, 3652 (1985) and in Biochem J. 257, 321 (1989).

p45 v-abl Kinase Assay (Val$^5$)-Angiotensin II phosphorylation was performed by incubation with 40 ng of purified abl-kinase and $(g-^{32}p)$-ATP, in 50 ml of buffer containing Tris-HCl 25 mM, Ph 8.0, $MgCl_2$ 10 Mm and dithiothreitol 0.1 Mm (kinase buffer). The reaction mixture was incubated for the indicated time at 300° C. and the reaction stopped by adding 50 ml of 5% trichloroacetic acid. After a brief incubation on ice, tubes were centrifuged. The supernatants were spotted on phosphocellulose paper squares (Whatman P-81) and washed extensively in acetic acid. The radioactivity bound to dried phosphocellulose squares was measured in a liquid scintillation counter. $IC_{50}$ values were. calculated from triplicated determinations of each experimental point. Each inhibitor was tested at concentrations ranging from 0 to 400 mg in the presence of fixed concentrations of peptide (2 mM) and ATP (50 mM).

In-vivo Assay
K562 cell Growth Inhibition Assay 1 ml of K562 cells, grown in suspension, were incubated for 66 h with or without 10% foetal calf serum in the presence of 1 mCi of [$^3$H]-Thymidine. Cells were harvested, washed three times in cold PBS and treated with 5% trichloroacetic acid for 5 min. on ice. After a wash in ethanol: ether 2:1, the DNA was extracted by 0.5 N NaOH for 2 h at room temperature. The extract was counted in a liquid scintillation counter. The inhibitory activity data for a representative compound according to the present invention, obtained both in the in-vitro p45 v-abl kinase assay and in the in-vivo human chronic myeloid leukemia K562 cell growth inhibition assay described above, are set out in Table 1.

TABLE 1

Inhibition of p-45 v-abl kinase and K562 cell growth

| | IC$_{50}$ (mM) | |
|---|---|---|
| | v-abl | K562 |
| 5-amino-3-[(7-azaindol-3-yl)methylen]-2-oxindole ditrifluoroacetate | 0.09 | 8.8 |
| 5-cyano-3-[(7-azaindol-3-yl)methylen]-2-oxindole | 0.98 | 2.52 |

In view of their high activity and low toxicity, the compounds of the invention can be used safely in medicine. For example, the approximate acute toxicity (LD$_{50}$) of the compounds of the invention in the mouse, determined by single administration of increasing doses and measured on the seventh day after the treatment was found to be negligible. The compounds of the invention can be administered in a variety of dosage forms, e.g. orally, in the form of tablets, capsules, sugar or film-coated tablets, liquid solutions or suspensions; rectally, in the form of suppositories; parenterally, e.g. intramuscularly, or by intravenous injection of infusion; or topically. The dosage depends on the age, weight, condition of the patient and administration route; for example, the dosage adopted for oral administration to adult humans may range from about 10 to about 150–200 mg per dose, from 1 to 5 time daily. Of course, these dosage regimens may be adjusted to provide the optimal therapeutic response.

The invention includes pharmaceutical compositions comprising a compound of formula (I) or a pharmaceutically acceptable salt thereof in association with a pharmaceutically acceptable excipient (which can be a carrier or diluent). The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylceluose or polyvinyl pyrrolidone; disaggregating agents, e.g. a starch, alginic acid, alginates or sodium starch glycolate, effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating or film-coating processes.

The liquid dispersion for oral administration may be e.g. syrups, emulsions and suspensions. The syrup may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride. The solutions for intravenous injections or infusion may contain as carrier, for example, sterile water or, preferable, they may be in the form of sterile aqueous, isotonic saline solutions.

The suppositories may contain, together with the active compound, a pharmaceutically acceptable carrier, e.g. cocoa-butter, polyethylene glycol, a polyoxyethylene sorbitan fatty acid ester surfactant or lecithin. Compositions for topical application, e.g. creams, lotions, or pastes, can be prepared by admixing the active ingredient with a conventional oleaginous or emulsifying excipient. A further object of the present invention is a combined method of treatment of cancer in mammals, including humans, in need of such treatment, said method comprising administering:

1) a compound of formula (I), or a pharmaceutically acceptable salt thereof, and
2) an additional antitumor agent, in amounts and close enough together in time sufficient to produce a therapeutically useful effect.

Object of the present invention is also to provide products containing a compound of formula (I), or a pharmaceutically acceptable salt, and an additional antitumor agent as a combined preparation for simultaneous, separate or sequential use in anti-cancer therapy.

The term "antitumor agent" is meant to comprise both a single antitumor drug and "cocktails" i.e. a mixture of such drugs, according to the clinical practice.

Antitumor agents that can be formulated with a compound of the invention or alternatively, can be administered in a combined method of treatment, are e.g. doxorubicin, daunomycin, epirubicin, idarubicin, etoposide, fluorouracil, melphalan, cyclophosphamide, bleomycin, vinblastine and mitomycin or a mixture of two or more thereof. The compounds of the invention can therefore be used in a treatment to ameliorate a cancer. They may be administered to a patient suffering from a cancer treatable with an antitumor agent, for example and anthracycline glycoside such as doxorubicin, daunomycin, epirubicin or idarubicin as mentioned above, together with the antitumor agent. A compound of the invention and an antitumor agent such as an anthracycline glycoside can be administered to improve the condition of a patient having a leukemia such as myeloblastic leukaemia, lymphoma, sarcoma, neuroblastoma, Wilm's tumor or malignant neoplasm of the bladder, breast, lung or thyroid.

The following examples illustrate but do not limit the invention:

EXAMPLE 1

5-sulfamoyl-3-[(7-azaindol-3-yl)methylen]-2-oxindole
(I, X$^4$=N, X$^1$=X$^2$=X$^3$=CH, R=d, R$^3$=5—SONH$_2$, R$^1$=R$^2$=H)

A solution of 3-formyl-7-azaindole (1.46 g, 10 mmol), 5-sulfamoyl-2-oxindole (2,122 g, 10 mmol) and piperidine (0,255 g, 3 mmol) in absolute ethanol (50 ml) was treated for 3 h at reflux. The reaction mixture was chilled to room temperature, the precipitate filtered, the residue washed with ice-cold ethanol and dried under vacuum. Almost pure title compound was so obtained in about 70% yield. Compounds of higher purity were obtained by crystallization from ethanol.

$C_{16}H_{11}N_4O_3S$ calcd: C 56.63 H 3.27 N 16.51 S 9.45
found: C 56.55 H 3.15 N 16.35 S 9.35
MS m/z 339.
IR cm[-1]: 3600–3100 (NH), 1655 (CO), 1610, 1550, 1540

According to the above described procedure and starting from the appropriate compounds of formula (II) and of formulae (a'), (b'), (c') and (d'), respectively, one can prepare the following compounds as single E- or Z-isomers, as well as their E,Z-mixtures:

2-cyano-3-(4-sulfo-7-azaindol-3-yl)acrylamide, sodium salt;
2-cyano-3-[(N,N-piperazinyl-4-sulfamoyl)-7-azaindol-3-yl) acrylamide;
2-cyano-3-(4-ureido-7-azaindol-3-yl) acrylamide;
2-cyano-3-(4-glyceroylamido-7-azaindol-3-yl) acrylamide;
2-cyano-3-[4-(3-piperidinopropionylamino)-7-azaindol-3-yl) acrylamide;
2-cyano-3-(4-mesylamino-7-azaindol-3-yl)acrylamide;
2-cyano-3-[4-(2,3-dihydroxypropoxy)-7-azaindol-3-yl] acrylamide;
2-cyano-3-(4-aminomethyl-7-azaindol-3-yl)acrylamide;
2-cyano-3-(4-amidinol-7-azaindol-3-yl)acrylamide;
2-cyano-3-(4-sulfo-7-azaindol-3-yl)thioacrylamide, sodium salt;
2-cyano-3-[(N,N-piperazinyl-4-sulfamoyl)-7-azaindol-3-yl)]thioacrylamide;
2-cyano-3-(4-ureido-7-azaindol-3-yl) thioacrylamide;
2-cyano-3-(4-glyceroylamido-7-azaindol-3-yl) thioacrylamide;
2-cyano-3-[4-(31piperidinopropionylamino)-7-azaindol-3-yl]thioacrylamide;
2-cyano-3-(4-mesylamino-7-azaindol-3-yl)thioacrylamide;
2-cyano-3-[4-(2,3-dihydroxy)propoxy-7-azaindoi-3-yl] thioacrylamide;
2-cyano-3-(4-aminomethyl-7-azaindol-3-yl)thioacrylamide;
2-cyano-3-(4-amidino-7-azaindol-3-yl)thioacrylamide;
2-cyano-3-(4-sulfo-7-azaindol-3-yl)acrylonitrile, sodium salt;
2-cyano-3-[(N,N-piperazinyl-4-sulfamoyl)-7-azaindol-3-yl]-acrylonitrile;
2-cyano-3-(4-ureido-7-axaindol-3-yl)acrylonitrile;
2-cyano-3-(4-glyceroylamido-7-azaindol-3-yl)-acrylonitrile;
2-cyano-3-[4-(3-piperidinopropionylamino)-7-azaindol-3-yl]acrylonitrile;
2-cyano-3-(4-mesylamino-7-azaindol-3-yl)acrylonitrile;
2-cyano-3-[4-(2,3-dihydroxpropoxy)-7-azaindol-3-yl] acrylonitrile;
2-cyano-3-(4-aminomethyl-7-azaindol-3-yl)acrylonitrile;
2-cyano-3-(4-amidinoi7-azaindol-3-yl)acrylonitrile;
3-[(71azaindol-3-yl)methylen]-2-oxindole-5-sulfonic acid, sodium salt;
5-(N,N-piperazinylsulfamoyl)-3-[(7-azaindol-3-yl)methylen]-2-oxindole;
5-[N,N-(4-hydroxyethyl)piperazinylsulfamoyl]-3-[(7-azaindol-3-yl)methylen]-2-oxindole;
5-diethanolamino-3-[(7-azaindol-3-yl)methylen]-2-oxindole;
5-ureido-3-[(7-azaindol-3-yl)methylen]-2-oxindole;
5-guanidino-3-[(7-azaindol-3-yl)methylen]-2-oxindole;
5-glyceroylamido-3-[(7-azaindol-3-yl)methylen]-2-oxindole;
5-(3-piperidino-propionylamino)-3-[(7-azaindol-3-yl)methylen]-2-oxindoledihydrochloride;
5-mesylamino-3-[(7-azaindol-3-yl)methylen]-2-oxindole;
5-(2,3-dihydroxypropoxy)-3-[(7-azaindol-3-yl)methylen]-2-oxindole;
5-glyceroyloxy-3-[(7-azaindol-3-yl)methylen]-2-oxindole;
3-[(7-azaindol-3-yl)methylen]-2-oxindol-5-yl phosphate;
5-aminomethyl-3-[(7-azaindol-3-yl)methylen]-2-oxindole;
5-amidino-3-[(7-azaindol-3-yl)methylen]-2-oxindole;
5-(2,3-dihydroxypropylamino)-3-[(7-azaindol-3-yl)methylen]-2-oxindole;
5-carbomethoxy-3-[(7-azaindol-3-yl)methylen]-21oxindole;
5-[4-(2-hydroxyethyl)-1-piperazinylmethyl]-3-[(7-azaindol-3-yl) methylen]-2-oxindole;
5-[N,N-4-(2-hydroxyethyl)piperazinylcarbamoyl]-3-(7-azaindol-3-yl)methylen]-2-oxindole;
5-glycoloyloxy-3-[(7-azaindol-3-yl)methylen]-2-oxindole;
5-amino-3-[(7-azaindol-3-yl)methylen]-2-oxindole, ditrifluoroacetate;
5-carboxy-3-[(7-azaindol-3-yl) methylen]-2-oxindole, piperidinium salt.
5-cyano-3-[(7-azaindol-3-yl) methylen]-2-oxindole;
$C_{17}H_{10}N_4O$ calcd: C 71.32 H 3.52 N 19.54
found: C 71.25 H 3.60 N 19.21
MS m/z 286.
NMR δ ppm: 6.89 (d=, J=8.1 Hz, 1H), 7.22 (dd, J=4.8 and 8.0 Hz, 1H), 7.49 (dd, J=8.1 and 1.7 Hz, 1H), 8.30 (m, 3H), 8.55 (dd, J=8.0 and 1.6 Hz, 1H), 9.42 (s, 1H), 10.9 (bs, 1H), 12.5 (bs, 1H).
5-carboethoxy-3-[(7-azaindol-3-yl)methylen]-2-oxindole.
$C_{19}H_{15}N_3O_3$ calcd: C 68.46 H 4.54 N 12.61
found: C 68.35 H 4.46 N 12.53
MS m/z 333.
NMR δ ppm (DMSO): 1.35 (t, J=7.2 Hz, 3H), 4.33 (g, J=7.2 Hz, 2H), 6.95 (d, J=7.9 Hz, 1H), 7.29 (dd, J=4.8 and 8.2 Hz, 1H), 7.82 (dd, J=7.9 and 1.7 Hz, 1H), 8.34 (dd, J=4.8 and 1.4 Hz, 1H), 8.36 (s, 1H), 8.52 (d, J=1.7 Hz., 1H), 8.75 (dd, J=8.2 and 1.4 Hz, 1H), 9.59 (s, 1H), 10.98 (s, 1H), 12.5 (bs, 1H).
5-carbobenzyloxy-3-[(7-azaindol-3-yl)methylen]-2-oxindole.
$C_{24}H_{17}N_3O_3$ calcd: C 72.90 H 4.33 N 10.63
found: C 72.85 H 4.21 N 10.45
MS m/z 395.
NMR δ ppm (DMSO): 5.22 (s, 2H), 5.37 (s, 2H), 6.94 (d, J=8.6 Hz, 1H), 6.99 (d, J=8.6 Hz, 1H), 7.1–7.6 (m, 6 Hz, 6 He), 7.8–8.0 (m, 3 He, 1 Hz), 8.14 (d, J=1.8 Hz, 1H), 8.2–8.4 (m, 2 He, 2 Hz), 8.57 (d, J=1.8 Hz, 1H), 8.74 (dd, J=1.5 and 7.9 Hz, 1H), 9.53 (s, 1H), 10.95 (s, 1H), 10.99 (s, 1H), 12.6 (bs, 1 He+1 Hz).
5-carbophenylethyloxy-3-[(7-azaindol-3-yl)methylen]-2-oxindole.

EXAMPLE 2

3-[(7-azaindol-3-yl)methylene]-2-oxindole-5-sulfonic acid
(I, $X^4$=N, $X^1$=$X^2$=$X^3$=CH, R=d, $R^3$=5—$SO_3H$, $R^1$=$R^2$=H)

A solution of 3-formyl-7-azaindoie (1.46 g, 0.010 mol) and 2-oxindole-5-sulfonic acid (2.55 g, 0.012 mol) in absolute ethanol (10 ml) was heated to reflux for 1 h. The reaction mixture was chilled with ice water, the precipitate filtered, the residue washed with ice-cooled ethanol and dried under vacuum. Almost pure titie compound was obtained in about 70% yield (2.389 g).

$C_{16}H_{11}N_3O_4S$ calcd: C 56.30 H 3.25 N 12.31 S 9.39
found: C 56.25 H 3.19 N 12.35 S 9.31

Ms m/z 341
IR cm$^{-1}$: 3600–3000 (NH), 1650 (CO), 1600, 1580, 1530 (C=C)

EXAMPLE 3

5-(2,3-dihydroxypropylamino)-3-[(7-azaindol-3-yl)methylene]-2-oxindole
(I, $X^4$=N, $X^1$=$X^2$=$X^3$=CH, R=d, $R^1$=$R^2$=H, $R^3$=NHCH$_2$CHOHCH$_2$OH)

To a stirred solution of 5-amino-3-[(7-azaindol-3-yl)methylen]-2-oxindole (2.773 g, 10 mmol) in methanol (30 ml) was added anhydrous methylammonium chloride (0.60 g, 10 mmol). Then sodium cyanoborohydride (0.378 g, 6 mmol) was added in portions. Finally, glyceraldehyde (0.901 g, 10 mmol) was added portionwise over 30 min and the solution stirred at room temperature for 50 h. Ice cold 6N HCl was added until gas evolution (HCN) stopped and the pH of the solution was 2. The methanol was evaporated in vacuo and the remaining aqueous solution was washed with CHCl$_3$. Solid KOH was added until the pH was 12. Solid NaCl was added to saturation and the solution extracted twice with CHCl$_3$. The CHCl$_3$ extracts were washed with saturated NaCl solution, dried over K$_2$CO$_3$ and evaporated. The residue was chromatographed on silica gel using CHCl$_3$—MeOH mixtures as eluant. Thus pure title compound was obtained in about 60% yield.

$C_{19}H_{18}N_4O_3$ calcd: C 65.13 H 5.18 N 15.99
found C 65.05 H 5,05 N 15.85
MS m/z 350.

EXAMPLE 4

5-glyceroylamido-3-[(7-azaindol-3-yl)methylene]-2-oxindole;
(I, $X^4$=N, $X^1$=$X^2$=$X^3$=CH, R=d, $R^1$=$R^2$=H, $R^3$=NHCOCHOHCH$_2$OH)

To a stirred solution of 5-amino-3-[(7-azaindol-3-yl)methylene]-2-oxindole (2.773 g, 10 mmol) and glyceric acid (1.061 g, 10 mmol) in benzene (200 ml) was added dicyclohexylcarbodiimide (2.063 g, 10 mmol). The resulting suspension was stirred for 1 h at 50°–60° C. and then for 3 days at room temperature. Then the N,N'-dicyclohexylurea was filtered off, the filtrate evaporated and the residue chromatographed on silica gel using CHCl$_3$—MeOH mixtures as eluant. Thus pure title compound was obtained in about 50% yield.

$C_{19}H_{16}N_4O_4$ calcd: C 62.63 H 4.43 N 15.38
found: C 62.55 H 4.35 N 15.40
MS m/z 364.

IR cm$^{-1}$: 3600–2500 (NH,OH), 1680 (CO), 1650 (CO), 1620 (amide), 1600, 1580, 1550.

EXAMPLE 5

5-mesylamino-3-[(7-azaindol-3-yl)methylene]-2-oxindole;
(I, $X^4$=N, $X^1$=$X^2$=$X^3$=CH, R=d, $R^1$=$R^2$=H; $R^3$=NHSO$_2$Me)

To a stirred solution of 5-amino-3-[(7-azaindol-3-yl)methylene]-2-oxindole (2.773 g, 10 mmol) in pyridine (10 ml) was added gradually mesylchloride (1.146 g, 10 mmol) at 0°–5° C. under cooling. The reaction mixture was stirred for about 5 h at 0°–5° C. and then for 15 h at room temperature. The mixture was poured onto an ice-water mixture, the precipitate filtered off, the residue washed thoroughly with water and then chromatographed on silica gel using CHCl$_3$—MeOH mixtures as eluant. Thus pure title compound was obtained in about 70% yield.

$C_{17}H_{14}N_4O_3S$ calcd: C 57.62 H 3.98 N 15.81 S 9.05
found: C 57.55 H 3.85 N 15.75 S 9.01
MS m/Z 354.

IR cm$^{-1}$: 3600–3000 (NH), 1650 (CO), 1600, 1580 (C=C).

EXAMPLE 6

5-guanidino-3-[(7-azaindol-3-yl)methylene]-2-oxindole;
(I, $X^4$=N $X^1$=$X^2$=$X^3$=CH, R=d $R^1$=$R^2$=H, $R^3$=NH—C(NH$_2$)=NH)

A mixture of 5-amino-3-[(7-azaindol-3-yl)methylene]-2-oxindole (2.773 g, 10 mmol) and sodium bicarbonate (0.168 g, 2 mmol) in refluxing ethanol (100 ml) was treated with 3,5-dimethylpyrazole-1-carboxamidine nitrate (3.018 g, 15 mmol) for 20 h. The solvent was removed from the cooled solution, and the residue was chromatographed on silica gel with gradient elution (1 to 5% EtOH in CHCl$_3$) to afford pure title compound in about 50% yield.

$C_{17}H_{14}N_6O$ calcd: C 64.14 H 4.43 N 26.40
found: C 64.10 H 4.35 N 26.30
MS m/z 318

IR cm$^{-1}$: 3800-3100 (NH), 1680 (C=NH), 1655 (CONH), 1620, 1600, 1520 (C=C).

EXAMPLE 7

5-ureido-3-[(7-azaindol-3-yl)methylene]-2-oxindole;
(I, $X^4$=N, $X^1$=$X^2$=$X^3$=CH, R=d, $R^1$=$R^2$=H, $R^3$=NHCONH$_2$)

A mixture of 5-amino-3-[(7-azaindol-3-yl)methylene]-2-oxindole (2.773 g, 10 mmol) in ice water (20 ml) are added 5N HCl (2 ml, 10 mmol) under stirring. Then the mixture was heated to 70°14 80° C., sodium cyanate (0.715 g, 11 mmol) was added portionwise and the stirring was continued for further 4 h at this temperature. After cooling the raw product was extracted with CHCl$_3$, the organic layer washed to neutrality with saline solution, dried and evaporated in vacuo. The residue was chromatographed on silica gel using CHCl$_3$—MeOH mixtures as eluant to give pure title compound in about 50% yield.

$C_{17}H_{13}N_5O_2$ calcd: C 63.95 H 4.10 N 21.93
found: C 63.88 H 3.95 N 21.85
MS m/z 319.

IR cm$^{-1}$: 3600–3100 (NH), 1660 (CO), 1650 (CO), 1620, 1590 (C=C)

EXAMPLE 8

5-(2,3-dihydroxypropoxy)-3-[(7-azaindol-3-yl)methylene]-2-oxindole;
(I, $X^4$=N $X^1$=$X^2$=$X^3$=CH, R=d, $R^1$=$R^2$=H, $R^3$=OCH$_2$CHOHCH$_2$OH)

To a solution of 5-hydroxy-3-[(7-azaindol-3-yl)methylene]-2-oxindole (2.773 g, 10 mmol) in toluene (100 ml) was added portionwise under nitrogen NaH 80% (0.300 g, 10 mmol). After the salification was complete 3-chloro-1,2-propane-diol (1.547 g, 14 mmol) was added and the mixture heated to reflux for 5 h. After cooling water was added, the organic phase washed and evaporated to dryness. The residue was submitted to flash chromatography using CHCl$_3$—MeOH mixtures as eluant to give pure title compound in about 70% yield.

$C_{19}H_{17}N_3O_4$ calcd: C 64.95 H 4.88 N 11.96
found: C 64.88 H 4.75 N 11.89
Ms m/z 351.

IR cm$^{-1}$: 3600–2600 (NH,OH), 1660 (CO), 1610, 1590, 1550 C=C).

EXAMPLE 9

5-glycoloyloxy-3-[(7 1azaindol-3-yl)methylene]-2-oxindole;

(I, $X^4$=N, $X^1$=$X^2$=$X^3$=CH, R=d, $R^1$=$R^2$=H, $R^3$=OCOCH$_2$OH)

To a stirred solution of 5-hydroxy-3-[(7-azaindol-3-yl)methylene]-2-oxindole (2.773 g, 10 mmol) in pyridine (10 ml) was added gradually glycoloyl chloride (0.945 g, 10 mmol) at 0°-5° C. under cooling. The reaction mixture was stirred for about 4 h at 0°-5° C. and then for 15 h at room temperature. The mixture was poured onto an ice-water mixture, the precipitate filtered off, the residue washed thoroughly with water and then chromatographed on silica gel using CHCl$_3$—MeOH mixtures as eluant. Thus pure title compound was obtained in about 60% yield.

$C_{18}H_{13}N_3O_4$ calcd: C 64.48 H 3.91 N 12.53
found C 64.35 H 3.85 N 12.45
MS m/z 335.
IR cm$^{-1}$: 3600–2600 (NH, OH), 1740 (CO), 1660 (CO), 1610, 1580.

EXAMPLE 10

5 3-[(7-azaindol-3-yl)methylene]-2-oxindol-5-yl phosphate (I, $X^4$=N, $X^1$=$X^2$=$X^3$=CH, R=d, $R^1$=$R^2$=H, $R^3$=OPO(OH)$_2$)

A mixture of 5-hydroxy-3-[(7-azaindol-3-yl)methylene]-2-oxindole (2.773 g, 10 mmol) and phosphoric acid 85% (13 g) and phosphorus pentoxide (10 g) was heated for 2 h at 60° C. The usual work up gave the title compound in about 50% yield.

$C_{16}H_{12}N_3PO_5$ calcd: C 53.79 H 3.39 N 11.76 P 8.67
found: C 53.65 H 3.35 N 11.69 P 8.55
MS m/z 357.

EXAMPLE 11

5-carbomethoxy-3-[(7-azaindol-3-yl)methylene]-2-oxindole (I, $X^4$=N, $X^1$=$X^2$=$X^3$=CH, R=d, $R^1$=$R^2$=H, $R^3$=5—COOMe)

A solution of 5-carboxy-3-[(7-azaindol-3-yl)methylene]-2-oxindole (3.053 g, 10 mmol), methanol (3.2 g, 0.1 mol) and H$_2$SO$_4$ 95% (1 g) in benzene (100 ml) was heated in a Soxhlet apparatus for 10 h. To dry the distillate continuously, the cap of the Soxhlet contained anhydrous MgSO$_4$. After cooling, water was added, the organic phase repeatedly washed with water and then evaporated under vacuum. Thus almost pure title compound was obtained in about 90% yield.

$C_{18}H_{13}N_3O_3$ calcd: C 67.71 H 4.10 N 13.16
found: C 67.65 H 4.05 N 13.01
MS m/z 319.
IR cm$^{-1}$: 3600–3200 (NH), 1720 (COOMe),1660 (CO), 1620, 1600, 1580.

5-carboethoxy-3-[(7-azaindol-3-yl)methylen]-2-oxindole;
5-carbobenzyloxy-3-[(7-azaindol-3-yl)methylen]-2-oxindole;
5-carbophenylethyloxy-3-[(7-azaindol-3-yl)methylen]-2-oxindole.

EXAMPLE 12

5-amidino-3-[(7-azaindol-3-yl)methylene]-2-oxindole hydrochloride (I, $X^4$=N, $X^1$=$X^2$=$X^3$=CH, R=d, $R^1$=$R^2$=H, $R^3$=C(NH$_2$)=NH)

To a solution of 5-cyano-3-[(7-azaindol-3-yl)methylene]-2-oxindole (2.863 g, 10 mmol) in anhydrous diethylether (100 ml) a stechiometric amount of ethanol (0.460 g, 10 mmol) was added and the solution was saturated with hydrogen chloride gas. The solution was kept overnight in the fridge in order to precipitate the iminoether hydrochloride salt. The precipitated iminoether hydrochloride was dissolved in ethanol (50 ml) to which was added an anhydrous alcoholic ammonia solution. Thereupon the solution was kept several days at room temperature and the precipitated little amount of NH$_4$Cl was filtered off. The solution was evaporated in vacuum, thus obtaining almost pure title compound.

$C_{17}H_{13}N_5O$·HCl calcd: C 60.09 H 4.15 N 20.61 Cl 10.43
found: C 59.95 H 4.05 N 20.55 Cl 10.33
MS m/z 339.

EXAMPLE 13

5-(4-hydroxyethyl-1-piperazinylmethyl)-3-[(7-azaindol-3-yl) methylene]-2-oxindole hydrochloride.

A mixture of 5-(chloromethyl)-3-[(7-azaindol-3-yl) methylene]-2-oxindole (3.098 g, 10 mmol), 4-hydroxyethyl-piperazine (2.604 g, 20 mmol) in 1N NaOH (20 ml, 20 mmol) was refluxed for 48 h. The cooled reaction mixture was extracted with ether, and the ether extract was shaken with diluted hydrochloric acid. The aqueous acid layer was made alkaline with potassium carbonate and extracted with ether. Addition of hydrogen chloride to the dried ether extract precipitated a crude hydrochloride which was crystallized twice from a mixture of methanol and ether.

$C_{23}H_{26}ClN_5O_2$ calcd: C 62.79 H 5.96 N 15.92 Cl 8.06
found: C 62.71 H 5.91 N 15.85 Cl 8.01
MS m/z 439.

EXAMPLE 14

5-[N,N-(4-hydroxyethyl)piperazinylcarbamoyl]-3-[(7-azaindol-3-yl) methylene]-2-oxindole (I, $X^4$=N, $X^1$=$X^2$=$X^3$=CH, R=d, $R^1$=$R^2$=H,

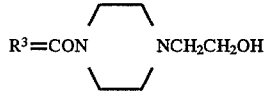

A mixture of 5-methoxycarbonyl-3-[(7-azaindol-3-yl) methylene]-2-oxindole (3.193 g, 10 mmol), 4-hydroxyethyl-piperazine (1.302 g, 10 mmol) and sodium methoxide (0.540 g, 10 mmol) in benzene (50 ml) was heated to reflux for 10 h. After cooling water was added cautiously, the organic phase was washed thoroughly with water and then evaporated under vacuum. The residue was submitted to column chromatography on silica gel using CHCl$_3$—MeOH mixtures as eluant. Thus pure title compound was obtained in about 60% yield.

$C_{23}H_{23}N_5O_3$ calcd: C 66.17 H 5.55 N 16.77
found C 66.09 H 5.47 N 16.58
MS m/z 417.
NMR δ ppm: 6.76 (d=, J=8.1 Hz, 1H), 7.25 (dd, J=4.7 and 8.1 Hz, 1H), 7.46 (dd, J=8.1 and 1.5 Hz, 1H), 8.13 (d, J=1.5 Hz, 1H), 8.20 (s, 1H), 8.33 (dd, J=4.7 and 1.5 Hz, 1H), 8.74 (dd, J=8.1 and 1.5 Hz, 1H), 9.54 (s, 1H), 10.63 (s, 1H), 12.4 (bs, 1H).

5-phenylcarbamoyl-3-[(7-azaindol-3-yl)methylen]-2-oxindole; 5-benzylcarbamoyl-3-[(7-azaindol-3-yl)methylen]-2-oxindole.

$C_{24}H_{18}N_4O_2$ calcd: C 73.08 H 9.60 N 14.20
found: C 72.95 H 4.51 N 14.05
MS m/z 394.

NMR δ ppm (DMSO): 4.51 (d, J=5.7 Hz, 2H), 6.89 (d, J=7.9 Hz, 1H), 7.1–7.4 (m, 6H), 7.74 (dd, J=7.9 and 1.7 Hz, 1H), 8.20 (s, 1H), 8.34 (dd, J=4.8 and 1.4 Hz, 1H), 8.40 (d, J=1.7 Hz, 1H), 8.60 (dd, J=8.2 and 1.4 Hz, 1H), 8.84 (t, J=5.7 Hz, 1H), 9.5 (s, 1H), 10.83 (s, 1H), 12.4 (bs, 1H).

EXAMPLE 15

3-[(7-azaindol-3-yl) methylene]-2-oxindole-5-sulfonic acid, sodium salt
(I, $X^4=N$, $X^1=X^2=X^3=CH$, R=d, $R^1=R^2=H$, $R^3$=5—$SO_3Na$)

To a solution of 3-[(7-azaindol-3-yl)methylene]-2-oxindole-5-sulfonic acid (3.414 g, 10 mmol) in 1N NaOH (10 ml, 10 mmol) was added isopropanol (30 ml) and the mixture was chilled under stirring to 0°–5° C. The precipitated sodium salt was filtered, washed with ice-cooled isopropanol and dried under vacuum.

$C_{16}H_{10}N_3O_4SNa$
calcd: C 52.89 H 2.77 N 11.57 S 8.82 Na 6.33
found: C 52.85 H 2.65 N.11.45 S 8.75 Na 6.25
MS m/z 363.

EXAMPLE 16

5-(3-piperidinopropionylamino)-3-[(7-azaindol-3-yl) methylen]-2-oxindole dihydrochloride
(I, $X^4=N$, $X^1=X^2=X^3=CH$, R=d, $R^1=R^2=H$,

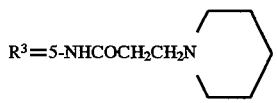
$R^3$=5-NHCOCH$_2$CH$_2$N

To a solution of 5-(3-piperidino)propionylamino-3-[(7-azaindol-3-yl)methylen]-2-oxindole (0.416 g, 1 mmol) in ethanol (10 ml) was added N NHCl (2 ml, 2 mmol) and the resulting mixture was evaporated to dryness under vacuum thus giving pure title compound in about 100% yield.

$C_{24}H_{27}N_5O_2Cl_2$ calcd: C 59.02 H 5.57 N 14.34 Cl14.52
found: C 58.95 H 5.45 N 14.27 Cl 14.60
MS m/z 488.

NMR δ ppm (DMSO): 1.3–1.9 (m, 6H), 2.9 (m, 4H), 3.33 (m, 2H), 3.42 (m, 2H), 6.80 (d, J=8.1 Hz, 1H), 7.26 (dd, J=1.8 and 8.1 Hz, 1H), 7.31 (dd, J=4.8 and 7.7 Hz, 1H), 7.98 (m, 2H), 8.37 (dd, J=1.1 and 4.8 Hz, 1H), 8.56 (dd; J=1.1 and 7.7 Hz, 1H), 9.52 (d, J=2.6 Hz, 1H), 10.17 (s, 1H), 10.2 (bs, 1H), 10.56 (s, 1H), 12.6 (bs, 1H).

EXAMPLE 17

5-amino-3-[(7-azaindol-3-yl) methylen]-2-oxindole ditrifluoroacetate;
(I, $X^4=N$, $X^1=X^2=X^3=CH$, R=d, R=$R^2=H$, $R^3$=5—$NH_2$)

To a solution of 5-amino-3-[(7-azaindol-3-yl)methylen]-2-oxindole (0.276 g, 1 mmol) in ethanol (10 ml) was added trifluoroacetic acid (0.228 g, 2 mmol) and the solution was concentrated under vacuum to a small volume. Ether was added to precipitate the salt, the mixture was ice-cooled, the solid was filtered off, washed With cold ether and essicated under vacuum. Thus almost pure title compound was obtained in about 90% yield.

$C_{20}H_{14}N_4F_6O_5$ calcd: C 47.63 H 2.80 N 11.11 F 22.60
found: C 47.55 H 2.75 N 11.05 F 22.62
MS m/z 504.

EXAMPLE 18

5-carboxy-3-[(7-azaindol-3-yl)methylen]-2-oxindole, piperidinium salt;
(I, $X^4=N$, $X^1=X^2=X^3=CH$, R=d, $R^1=R^2=H$, $R^3$=5—COOH)

To a solution of 5-carboxy-3-[(7-azaindol-3-yl)methylen]-2-oxindole (0.305 g, 1 mmol) in ethanol (10 ml) was added piperidine (0.085 g, 1 mmol) and the mixture was concentrated under vacuum to a small volume. To the ice-cooled mixture ether was added, the precipitate filtered off, washed with ice-cooled ether and dried under vacuum. Thus almost pure title compound was obtained in about 80% yield.

$C_{22}H_{22}N_4O_3$ calcd: C 67.68 H 5.68 N 14.35
found: C 67.61 H 5.55 N 14.20
MS m/z 390.

NMR δ ppm (DMSO): 1.52 (m, 6H), 2.89 (m, 4H), 6.82 (d, J=7.9 Hz, 1H), 7.25 (dd, J=7.9 and 4.6 Hz, 1H), 7.77 (dd, J=7.9 and 1.5 Hz, 1H), 8.21 (s, 1H), 8.32 (dd, J=4.6 and 1.5 Hz, 1H), 8.43 (d, J=1.5 Hz, 1H), 8.71 (dd, J=7.9 and 1.5 Hz, 1H), 9.52 (s, 1H), 10.7 (bs, 1H).

EXAMPLE 19

7-azaindol-3-carboxaldehyde
(II, $X^4=N$, $X^1=X^2=X^3=CH$, $R^1=R^2=H$)

A solution of 7-azaindole (23.6 g, 0.20 mol) and hexamethylenetetramine (42 g, 0.30 mol) in 33% acetic acid (84 g, 1.4 mol and 168 ml $H_2O$) was refluxed for 6 h. The resulting clear yellow solution was diluted with water, and the product was allowed to crystallize in the refrigerator overnight. Recrystallization of the crude product from water gave almost pure title compound in 50% yield 14.9 g). m.p. 216°–218° C.

$C_8H_6N_2O$ requires: C 65.74 H 4.13 N 19.17
found: C 65.65 H 4.05 N 19.05
MS m/z 146

The isomeric 4-, 5- or 6-azaindol-3-carboxaldehydes can be obtained by the above described procedure starting from the 4-, 5- or 6-azaindoles, respectively.

EXAMPLE 20

Tablets each weighing 0.150 g and containing 25 mg of the active substance, can be manufactured as follows: Composition (for 10,000 tablets):

| | |
|---|---|
| 5-amino-3-[(7-azaindol-3-yl)methylen]-2-oxindole ditrifluoroacetate | 250 g |
| Lactose | 800 g |
| Corn starch | 415 g |
| Talc powder | 30 g |
| Magnesium stearate | 5 g |

The 5-amino-3-[(7-azaindol-3-yl)methylen]-2-oxindole ditrifluoroacetate, the lactose and half the corn starch are mixed; the mixture is then forced through a sieve of 0.5 mm mesh size.

Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate are added carefully mixed and processed into tablets.

EXAMPLE 21

Capsules, each dosed at 0.200 g and containing 20 mg of the active substance can be prepared. Composition for 500 Capsules:

| | |
|---|---|
| 3-[(7-azaindol-3-yl)methylene]-2-oxindole-5-sulfonic acid, sodium salt | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

We claim:

1. A compound of formula (I)

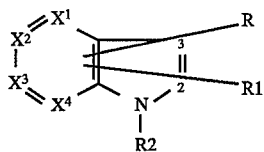

wherein one of the groups $X^1$, $X^2$, $X^3$ and $X^4$ is N and the others are CH; R is a group of formula (a), (b), (c) or (d)

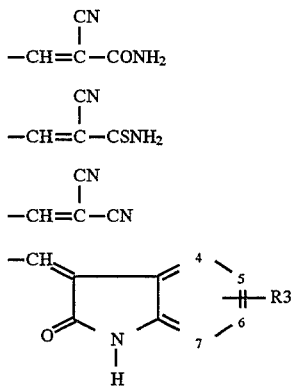

each of $R^1$ and $R^3$ independently is hydrogen, amino, carboxy, cyano, —$SO_3R^4$, —$SO_2NHR^5$,

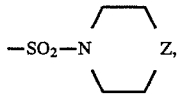

—$COOR^6$, —$CONH(CH_2)_oPh$, —$CONHCH_2(CHOH)_nCH_2OH$,

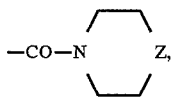

—$N(CH_2CH_2OH)_2$, —$NHCH_2(CHOH)_nCH_2OH$, $NHCONH_2$, —$NHC(NH_2)=NH$, —NHCO$(CHOH)_nCH_2OH$,

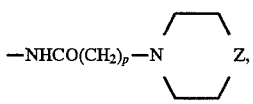

—$NHSO_2R^7$, $OCH_2(CHOH)_nCH_2OH$, —OOC$(CHOH)_nCH_2OH$, —$OPO(OH)_2$, —$OCH_2SO_2NH_2$, —$CH_2NH_2$, —$C(NH_2)=NH$, —$CH_2NHC(NH_2)$ =NH,

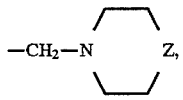

—$CH_2OH$, —$CH_2OOC(CHOH)_nCH_2OH$, —$CH_2OPO(OH)_2$, —$PO(OH)_2$;

$R^2$ is H, $C_1$-$C_6$ alkyl, $C_2$-$C_6$ alkanoyl, —$CH_2OH$, —$CH_2CH_2CONH_2$, —$SO_2Me$, —$COCH_2SO_2NH_2$;

$R^4$ is H, —$CH_2(CHOH)_nCH_2OH$, $C_1$-$C_6$ alkyl;

$R^5$ is H, $C_1$-$C_6$ alkyl, —$CH_2(CHOH)_nCH_2OH$, —$(CH_2)_mNMe_2$;

$R^6$ is $C_1$-$C_6$ alkyl unsubstituted or substituted by phenyl, —$CH_2(CHOH)_nCH_2OH$;

$R^7$ is Me, —$C_6H_4Me$;

Z is $CH_2$, O, NH, $NCH_2CH_2OH$;

n is 0 or 1;

m is 2 or 3;

o is 0, 1, 2 or 3;

p is 1, 2 or 3;

provided that when R is (a), (b), or (c) then $R^1$ is not H and when R is (d) then one of $R^1$ and $R^3$ is not H; and the pharmaceutically acceptable salts thereof.

2. A compound of formula (I), according to claim 1, wherein:

R is as defined in claim 1 and is linked in position 2 or 3 of the azaindole ring;

$R^2$ is hydrogen or $C_1$-$C_4$ alkyl;

each of $R^1$ and $R^3$ independently is hydrogen, amino, carboxy, cyano —$SO_3H$, —$SO_2NH_2$,

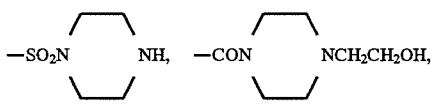

—COOME, —N$(CH_2CH_2OH)_2$, —NH—$CH_2$—CHOH—$CH_2OH$, —$NHCONH_2$, —$NHC(NH_2)=NH$, —$NHCOCHOHCH_2OH$,

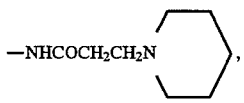

—$NHSO_2Me$, —$OCH_2CHOHCH_2OH$, —OOC—$CH_2OH$, —$OOCCHOHCH_2OH$, —$OPO(OH)_2$, —$CH_2NH_2$, —$C(NH_2)=NH$,

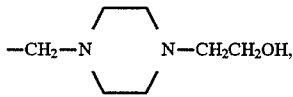

—$CH_2OH$, —$CH_2PO(OH)_2$, —$PO(OH)_2$, provided that when R is (a), (b) or (c) then $R^1$ is not hydrogen and when R is (d) then one of $R^1$ and $R^3$ is not hydrogen and the pharmaceutically acceptable salt thereof.

3. A compound of formula according to claim 1, wherein:

R is as defined above and is linked in position 3 of the azaimdole ring;

$R^2$ is hydrogen;

each of $R^1$ and $R^3$ independently is hydrogen, amino, carboxy, cyano, —$SO_3H$, —$SO_2NH_2$,

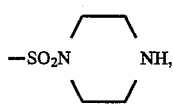

—N(CH₂CH₂OH)₂, —NHCONH₂, —NHC(NH₂)=NH,

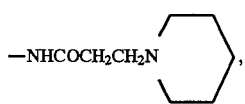

—NHSO₂Me, —OCH₂CHOHCH₂OH, —OOCCHOHCH₂OH, —CH₂NH₂, —C(NH₂)=NH, —CH₂OH, —PO(OH)₂, and R³ is preferably linked at position 5 of the oxindole ring; provided that when R is (a), (b), (c) then R¹ is not hydrogen and when R is (d) then one of R¹ and R³ is not hydrogen and the pharmaceutically acceptable salt thereof.

4. A compound selected from a group consisting of the following compounds, which, when appropriate, may be either Z- or E-diastereomers or Z,E-mixtures of said diastereomers:

2-cyano-3(4-sulfo-7-azaindol-3-yl)acrylamide, sodium salt;
2-cyano-3-[(N,N-piperazinyl-4-sulfamoyl)-7-azaindol-3-yl] acrylamide;
2-cyano-3-(4-ureido-7-azaindol-3-yl)acrylamide;
2-cyano-3-(4-glyceroylamido-7-azaindol-3-yl) acrylamide;
2-cyano-3-[4-(3-piperidinopropionylamino)-7-azaindol-3-yl]acrylamide;
2-cyano-3-(4-mesylamino-7-azaindol-3-yl)acrylamide;
2-cyano-3-[4-(2,3-dihydroxypropoxy)-7-azaindol-3-yl] acrylamide;
2-cyano-3-(4-aminomethyl-7-azaindol-3-yl) acrylamide;
2-cyano-3-(4-amidino-7-azaindol-3-yl)acrylamide;
2-cyano-3-(4-sulfo-7-azaindol-3-yl)thioacrylamide, sodium salt;
2-cyano-3-[(N,N-piperazinyl-4-sulfamoyl)-7-azaindol-3-yl] thioacrylamide;
2-cyano-3-(4-ureido-7-azaindol-3-yl)thioacrylamide;
2-cyano-3-(4-glyceroylamldo-7-azaindol-3-yl) thiolacrylamide;
2-cyano-3-[4-(3-piperidinopropionylamino)-7-azaindol-3-yl]thiacrylamide;
2-cyano-3-(4-mesylamino-7-azaindol-3-yl) thioacrylamide;
2-cyano-3-[4-(2,3-dihydroxypropoxy)-7-azaindol-3-yl] thioacrylamide;
2-cyano-3-(4-aminomethyl-7-azaindol-3-yl) thioacrylamide;
2-cyano-3-(4-amidino-7-azaindol-3-yl) thioacrylamide;
2-cyano-3-(4-sulfo-7-azaindol-3-yl)acrylonitrile, sodium salt;
2-cyano-3-[(N,N-piperazinyl-4-sulfamoyl)-7-azaindol-3-yl] acrylonitrile;
2-cyano-3-(4-ureido-7-azaindol-3-yl)acrylonitrile;
2-cyano-3-(4-glyceroylamidol-7-azaindol-3-yl) acrylonitrile;
2-cyano-3-[(4-(3-piperidinopropiolnylamino)-7-azaindol-3-yl]acrylonitrile;
2-cyano-3-(4-mesylamino-7-azaindol-3-yl) acrylonitrile;
2-cyano-3-[4-(2,3-dihydroxypropoxy)-7-azaindol-3-yl] acrylonitrile;
2-cyano-3-(4-aminomethyl-7-azaindol-3-yl) acrylonitrile;
2-cyano-3-(4-amidino-7-azaindol-3-yl)acrylonitrile;
3-[(7-azaindol-3-yl)methylen]-2-oxindole-5-sulfonic acid, sodium salt;
5-sulfamoyl-3-[(7-azaindol-3-yl)methylen]-2-oxindole;
5-(N,N-piperazinylsulfamoyl)-3-[(7-azaindol-3-yl) methylen]-2-oxindole;
5-[N,N-[4-(2-hydroxyethyl)piperazinylsulfamoyl]-3-[(7-azaindol-3-yl)methylen]-2-oxindole;
5-diethanolamino-3-[(7-azaindol-3-yl)methylen]-2-oxindole;
5-ureido-3-[(7-azaindol-3-yl)methylen]-2-oxindole;
5-guanidino-3-[(7-azaindol-3-yl)methylen]-2-oxindole;
5-glyceroylamido-3-[(7-azaindol-3-yl)methylen]-2-oxindole;
5-(3-piperidinopropionylamino)-3-[(7-azaindol-3-yl) methylen]-2-oxindole, dihydrochloride;
5-mesylamino-3-[(7-azaindole-3-yl)methylen]-2-oxindole;
5-(2,3-dihydroxypropoxy)-3-[(7-azaindol-3-yl)-methylen]-2-oxindole;
5-glyceroyloxy-3-[(7-azaindol-3-yl)methylen]-2-oxindole;
3-[(7-azaindol-3-yl)methylen]-2-oxindol-5-yl-phosphate;
5-aminomethyl-3-[(7-azaindol-3-yl)methylen]-2-oxindole;
5-amidino-3-[(7-azaindol-3-yl)methylen]-2-oxindole;
5-(2,3-dihydroxypropylamino)-3-[(7-azaindol-3-yl) methylen]-2-oxindole;
5-carbomethoxy-3-[(7-azaindol-3yl)methylen]-2-oxindole;
5-[4-(2-hydroxyethyl)-1-piperazinylmethyl)-3-[(7-azaindol-3-yl)methylen]-2-oxindole;
5-[N,N-[4-(2-hydroxyethyl)piperazinylcarbamoyl]-3-[7-azaindoi-3-yl)methylen]-2-oxindole;
5-glycoloyloxy-3-[(7-azaindol-3-yl)methylen]-2-oxindole;
5-amino-3-[(7-azaindol-3-yl)methylen]-2-oxindole, ditrifluoroacetate;
5-carboxy-3-[(7-azaindol-3-yl)methylen]-2-oxindole, piperidinium salt;
5-cyano-3-[(7-azaindoi-3-yl)methylen]-2-oxindole;
5-carboethoxy-3-[(7-azaindoi-3-yl)methylen]-2-oxindole;
5-carbobenzyloxy-3-[(7-azaindol-3-yl)methylen]-2-oxindole;
5-carbophenylethyloxy-3-[(7-azaindol-3-yl)methylen]-2-oxindole;
5-phenylcarbamoyl-3-[(7-azaindol-3-yl)methylen]-2-oxindole;
5-benzylcarbamoyl-3-[(7-azaindol-3-yl)methylen]-2-oxindole;

as well as the free compounds corresponding to the above listed salified compounds and the pharmaceutically acceptable salts of the above listed free compounds.

5. A process for preparing a compound of formula (I), according to claim 1 or a pharmaceutically acceptable salts thereof, comprising:

a) N-alkylation of a compound of formula (III)

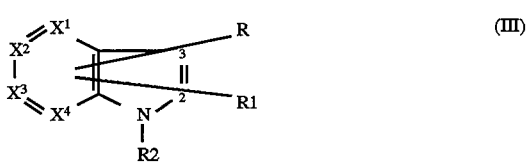

wherein either R¹ and R³ are both amino or one of R¹ and R³ is amino and the other is hydrogen, if it is present, and X¹, X², X³, X⁴, R and R² are as defined in claim 1, thus obtaining a compound of formula (I) wherein either R¹ and R³ are both —N(CH₂CH₂OH)₂ or —NHCH₂(CHOH)ₙCH₂OH, or one is —N(CH₂CH₂OH)₂ or —NHCH₂(CHOH)ₙCH₂OH and the other is hydrogen, if it is present, and n, X¹, X², X³, X⁴, R and R₂ are as defined in claim 1; or b) N-acylation of a compound of formula (III) wherein either $R^1$ and $R^3$ are both amino or one of $R^1$ and $R^3$ is amino and the other is hydrogen, if it is present, and $X^1$, $X^2$, $X^3$, $X^4$, R and $R^2$ are as defined in claim 1, thus obtaining a compound of formula (I) wherein either $R^1$ and $R^3$ are both —NHCO(CHOH)$_n$CH$_2$OH or

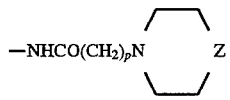

or one is —NHCO(CHOH)$_n$CH$_2$OH or

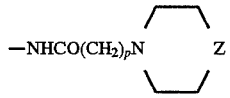

and the other is hydrogen, if it is present, n, p, Z, $X^1$, $X^2$, $X^3$, $X^4$, R and $R^2$ are as defined in claim 1; or c) N-sulfonylation of a compound of formula (III) wherein either $R^1$ and $R^3$ are both amino or one of $R^1$ and $R^3$ is amino and the other is hydrogen, if it is present, and $X^1$, $X^2$, $X^3$, $X^4$, R and $R^2$ are as defined in claim 1, thus obtaining a compound of formula (I) wherein either $R^1$ and $R^3$ are both —NHSO$_2$R$^7$ or one of $R^1$ and $R^3$ is —NHSO$_2$R$^7$ and the other is hydrogen, if it is present, and $R^7$, $X^1$, $X^2$, $X^3$, $X^4$, R and are as defined in claim 1; or d) N-amidination of a compound of formula (III) wherein either $R^1$ and $R^3$ are both amino or one of $R^1$ and $R^3$ is amino and the other is hydrogen, if it is present and $X^1$, $X^2$, $X^3$, $X^4$, R and $R^2$ are as defined in claim 1, thus obtaining a compound of formula (I) wherein either $R^1$ and $R^3$ are both —NHC(NH$_2$)=NH or one of $R^1$ and $R^3$ is —NHC(NH$_2$)=NH and the other is hydrogen, if it is present, and $X^1$, $X^2$, $X^3$, $X^4$, R and $R^2$ are as defined in claim 1; or e) N-carbamoylation of a compound of formula (III) wherein either $R^1$ and $R^3$ are both amino or one of $R^1$ and $R^3$ is amino and the other is hydrogen, if it is present, and $X^1$, $X^2$, $X^3$, $X^4$, R and $R^2$ are as defined in claim 1, thus obtaining a compound of formula (I) wherein either $R^1$ and $R^3$ are both, —NHCONH$_2$ or one of $R^1$ and $R^3$ is —NHCONH$_2$ and the other is hydrogen, if it is present, and $X^1$, $X^2$, $X^3$, $X^4$, R and $R^2$ are aS defined in claim 1; or f) O-alkylation of a compound of formula (III) wherein either $R^1$ and $R^3$ are both hydroxy or one of $R^1$ and $R^3$ is hydroxy and the other is hydrogen, if it is present, and $X^1$, $X^2$, $X^3$, $X^4$, R and $R^2$ are as defined in claim 1, thus obtaining a compound of formula (I) wherein either $R^1$ and $R^3$ are both —OCH$_2$(CHOH)$_n$CH$_2$OH or —OCH$_2$SO$_2$NH$_2$ or one of $R^1$ and $R^3$ is —OCH$_2$(CHOH)$_n$CH$_2$OH or —OCH$_2$SO$_2$NH$_2$ and the other is hydrogen, if it is present, and n, $X^1$, $X^2$, $X^3$, $X^4$,R and $R^2$ are as defined in claim 1; or g) O-acylation of a compound of formula (III) wherein either $R^1$ and $R^3$ are both hydroxy or one of $R^1$ and $R^3$ is hydroxy and the other is hydrogen, if, it is present, and $X^1$, $X^2$, $X^3$, $X^4$, R and $R^2$ are as defined in claim 1, thus obtaining a compound of formula (I) wherein either $R^1$ and $R^3$ are both —OOC(CHOH)$_n$CH$_2$OH or one of $R^1$ and $R^3$ is —OOC(CHOH)$_n$CH$_2$OH and the other is hydrogen, if it is present, and n, $X^1$, $X^2$, $X^3$, $X^4$, R and $R^2$ are as defined in claim 1; or h) O-phosphorylation of a compound of formula (III) wherein either $R^1$ and $R^3$ are both hydroxy or one of $R^1$ and $R^3$ is hydroxy and the other is hydrogen, if it is present, and $X^1$, $X^2$, $X^3$, $X^4$, R and $R^2$ are as defined in claim 1, thus obtaining a compound of formula (I) wherein either $R^1$ and $R^3$ are both —OPO(OH)$_2$ or one of $R^1$ and $R^3$ is —OPO(OH)$_2$ and the other is hydrogen, if it is present, and $X^1$, $X^2$, $X^3$, $X^4$, R and $R^2$ are as defined in claim 1; or i) esterification of a compound of formula (III) wherein either $R^1$ and $R^3$ are both carboxy or one of $R^1$ and $R^3$ is carboxy and the other is hydrogen, if it is present, and $X^1$, $X^2$, $X^3$, $X^4$, R and $R^2$ are as defined in claim 1, thus obtaining a compound of formula (I) wherein either $R^1$ and $R^3$ are both —COOR$^6$ or one of $R^1$ and $R^3$ is —COOR$^6$ and the other is hydrogen if it is present and $R^6$, $X^1$, $X^2$, $X^3$, $X^4$, R and $R^2$ are as defined in claim 1; or k) ammonia addition to a compound of formula (III) wherein either $R^1$ and $R^3$ are both —C≡N or one of $R^1$ and $R^3$ is —C≡N and the other is hydrogen, if it is present, and $X^1$, $X^2$, $X^3$, $X^4$, R and $R^2$ are as defined in claim 1, thus obtaining a compound of formula (I) wherein either $R^1$ and $R^3$ are both —C(NH$_2$)=NH of one of $R^1$ and $R^3$ is —C(NH$_2$)=NH and the other is hydrogen, if it is present, and $X^1$, $X^2$, $X^3$, $X^4$, R and $R^2$ are as defined in claim 1; or l) amination of a compound of formula (III) wherein either $R^1$ and $R^3$ are both —CH$_2$Cl or one of $R^1$ and $R^3$ is —CH$_2$Cl and the other is hydrogen, if it is present, and $X^1$, $X^2$, $X^3$, $X^4$, R and $R^2$ are as defined in claim 1, thus obtaining a substituted compound of formula (I) wherein either $R^1$ and $R^3$ are both

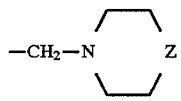

or one of $R^1$ and $R^3$ is

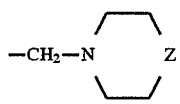

and the other is hydrogen, if it is present, and Z, $X^1$, $X^2$, $X^3$, $X^4$, R and $R^2$ are as defined in claim 1;

and/or conversion of a compound of formula (I) into another compound of formula (I) and/or optional salification of a compound of formula (I) or conversion of a salt into the corresponding free compound of formula (I) and/or, if desired, separation of a mixture of isomers into the single isomers.

6. A pharmaceutical composition containing a suitable carrier.and/or diluent and, as an active principle, a compound of formula (I) according to claim 1 or a pharmaceutically acceptable salt thereof.

7. A compound of formula (I) according to claim 1, or a pharmaceutically acceptable salt thereof, for use as a tyrosine kinase inhibitor.

8. Products containing a compound formula (I), according to claim 1, or a pharmaceutically acceptable salt thereof, and an antiltumor agent as a combined preparation for simultaneous, separate or sequential use in anti-cancer therapy.

9. A method of inhibiting tyrosine kinase activity comprising contacting cells having receptors which display tyrosine kinase activity with a compound as claimed in claim 1 in an amount effective to inhibit tyrosine kinase activity.

10. A method of treating pathological proliferation disorders in mammals, said disorders being selected from the group consisting of leukemia and psoriasis administering to a mammal in need thereof a pharmaceutically effective amount of a compound as claimed in claim 1.

* * * * *